United States Patent
Masse

(10) Patent No.: US 10,993,765 B2
(45) Date of Patent: May 4, 2021

(54) TEMPERATURE MEASUREMENT OF ELECTRICALLY CONDUCTIVE FLUIDS

(71) Applicant: Smith & Nephew, Inc., Austin, TX (US)

(72) Inventor: Daniel B. Masse, Windham, NH (US)

(73) Assignee: Smith & Nephew, Inc., Austin, TX (US)

(*) Notice: Subject to any disclaimer, the term of this patent is extended or adjusted under 35 U.S.C. 154(b) by 445 days.

(21) Appl. No.: 15/574,013

(22) PCT Filed: Jun. 29, 2016

(86) PCT No.: PCT/US2016/040023
§ 371 (c)(1),
(2) Date: Nov. 14, 2017

(87) PCT Pub. No.: WO2017/004160
PCT Pub. Date: Jan. 5, 2017

(65) Prior Publication Data
US 2018/0289412 A1  Oct. 11, 2018

Related U.S. Application Data

(60) Provisional application No. 62/186,523, filed on Jun. 30, 2015.

(51) Int. Cl.
*A61B 18/00* (2006.01)
*A61B 18/14* (2006.01)
*A61B 18/12* (2006.01)

(52) U.S. Cl.
CPC ........ *A61B 18/148* (2013.01); *A61B 18/1206* (2013.01); *A61B 18/1402* (2013.01);
(Continued)

(58) Field of Classification Search
CPC .............. A61B 18/042; A61B 18/1206; A61B 18/1402; A61B 18/148;
(Continued)

(56) References Cited

U.S. PATENT DOCUMENTS 5,630,426 A * 5/1997 Eggers ................. A61B 5/0531
600/395
5,853,409 A  12/1998 Swanson et al.
(Continued)

FOREIGN PATENT DOCUMENTS

| EP | 1080680 | 3/2001 |
|---|---|---|
| EP | 2789305 | 10/2014 |

(Continued)

OTHER PUBLICATIONS

Search Report and Written Opinion for PCT/US2016/040023 dated Sep. 30, 2016, 14 pages.

*Primary Examiner* — Jaymi E Della
*Assistant Examiner* — Rachel A. Vierra
(74) *Attorney, Agent, or Firm* — Norman F. Hainer, Jr.

(57) ABSTRACT

A method is disclosed including immersing electrodes disposed on a distal end of an electrosurgical wand, the immersing in a cavity defined within walls of a first material, the cavity comprising a conductive fluid different than the first material, and the electrodes comprising a first electrode and a second electrode. The method further includes applying a voltage across the first electrode and the second electrode, the first and second electrode spaced apart on the distal end of the wand such that the conductive fluid resides between the first and second electrodes. The method further includes measuring an impedance of the conductive fluid between the first and second electrodes; and determining temperature of the conductive fluid based on the measured impedance. The method further includes forming plasma proximate to an active electrode distinct from the first and (Continued)

second electrode, the plasma created based on voltage applied to the active electrode.

18 Claims, 8 Drawing Sheets

(52) U.S. Cl.
CPC ............ *A61B 2018/00083* (2013.01); *A61B 2018/00565* (2013.01); *A61B 2018/00583* (2013.01); *A61B 2018/00642* (2013.01); *A61B 2018/00666* (2013.01); *A61B 2018/00791* (2013.01); *A61B 2018/00803* (2013.01); *A61B 2018/00875* (2013.01); *A61B 2018/126* (2013.01); *A61B 2018/128* (2013.01); *A61B 2218/007* (2013.01)

(58) Field of Classification Search
CPC .......... A61B 2017/00973; A61B 2018/00565; A61B 2018/00583; A61B 2018/00708; A61B 2018/00791; A61B 2018/00803; A61B 2018/00875; A61B 2217/128; A61B 2217/007
See application file for complete search history.

(56) References Cited

U.S. PATENT DOCUMENTS

| | | | |
|---|---|---|---|
| 5,891,134 A * | 4/1999 | Goble | .............. A61B 18/08 606/191 |
| 6,053,912 A | 4/2000 | Panescu et al. | |
| 6,113,591 A | 9/2000 | Whayne et al. | |
| 6,149,647 A | 11/2000 | Tu et al. | |
| 6,217,574 B1 | 4/2001 | Webster, Jr. | |
| 6,241,724 B1 | 6/2001 | Fleischman et al. | |
| 6,391,024 B1 * | 5/2002 | Sun | .................. A61B 18/1206 606/34 |
| 6,402,742 B1 | 6/2002 | Blewett et al. | |
| 6,461,354 B1 | 10/2002 | Olsen et al. | |
| 6,837,884 B2 | 1/2005 | Woloszko | |
| 7,347,859 B2 | 3/2008 | Garabedian et al. | |
| 2007/0167943 A1 | 7/2007 | Janssen et al. | |
| 2008/0082092 A1 | 4/2008 | McPherson | |
| 2008/0082097 A1 | 4/2008 | McPherson | |
| 2008/0147060 A1 | 6/2008 | Choi | |
| 2008/0161797 A1 | 7/2008 | Wang et al. | |
| 2008/0243117 A1 | 10/2008 | Sharps et al. | |
| 2008/0281311 A1 | 11/2008 | Dunning | |
| 2009/0030477 A1 * | 1/2009 | Jarrard | ............... A61B 18/1206 607/42 |
| 2010/0152726 A1 * | 6/2010 | Cadouri | ............. A61B 18/1233 606/35 |
| 2011/0077641 A1 | 3/2011 | Dunning | |
| 2011/0270242 A1 * | 11/2011 | Marion | ................ A61B 18/148 606/35 |
| 2016/0022349 A1 * | 1/2016 | Woloszko | ............ A61B 18/042 606/34 |

FOREIGN PATENT DOCUMENTS

| | | |
|---|---|---|
| WO | 9600039 | 1/1996 |
| WO | 9634570 | 11/1996 |
| WO | WO03024506 | 3/2003 |

* cited by examiner

TEMPERATURE MEASUREMENT OF ELECTRICALLY CONDUCTIVE FLUIDS

CROSS-REFERENCE TO RELATED APPLICATIONS

This application claims the benefit of U.S. Provisional Application No. 62/186,523 entitled "Temperature Measurement of Electrically Conductive Fluids," filed Jun. 30, 2015 and PCT Application No. PCT/US2016/040023 entitled "Temperature Measurement of Electrically Conductive Fluids," filed Jun. 29, 2016. Each related application is incorporated by reference herein in its entirety.

BACKGROUND

Electrosurgical systems are used by physicians to perform specific functions during surgical procedures. Particular electrosurgical procedures may remove several different tissue types. For example, procedures involving the knee or shoulder may remove portions of cartilage, meniscus, and free floating and/or trapped tissue. During particular electrosurgical procedures, for example, arthroscopic joint surgery, when a radio frequency (RF) ablation or coagulation probe is used, the saline fluid in the joint can be heated by the RF probe. High saline temperatures can damage living tissue.

Any advance that achieves effective results without damaging living tissue, would provide a competitive advantage.

SUMMARY

A method is disclosed comprising immersing electrodes disposed on a distal end of an electrosurgical wand, the immersing in a cavity defined within walls of a first material, the cavity comprising a conductive fluid different than the first material, and the electrodes comprising a first electrode and a second electrode. The method further comprises applying a voltage across the first electrode and the second electrode where the first and second electrodes are spaced apart on the distal end of the wand such that the conductive fluid resides between the first and second electrode. The method further comprises measuring an impedance of the conductive fluid between the first and second electrodes and determining temperature of the conductive fluid based on the measured impedance.

Additionally, an electrosurgical system is disclosed comprising an electrosurgical wand comprising an active electrode disposed on a distal end of the electrosurgical wand. The electrosurgical wand further comprises a return electrode disposed on the distal end of the electrosurgical wand, where the return electrode is disposed proximally from the active electrode. The electrosurgical wand further comprises a measurement electrode disposed at the distal end of the electrosurgical wand, where the measurement electrode is distinct from both the active and the return electrodes and where the measurement electrode is exposed on an outside surface of the electrosurgical wand. The electrosurgical wand further comprises an insulator disposed between a portion of the return electrode and the measurement electrode.

The electrosurgical system further comprises an electrosurgical controller electrically coupled to the electrosurgical wand, the electrosurgical controller comprising a processor; a memory coupled to the processor; and an electrical generator operatively coupled to the processor. The electrical generator defines an active terminal, an impedance terminal, and a return terminal, where the impedance terminal is coupled to the measurement electrode, the return terminal is coupled to the return electrode, and the active terminal is coupled to the active electrode. The electrical is configured to provide controllable voltage to the electrodes. The memory of the electrosurgical controller stores a program that, when executed by the processor, causes the processor to measure impedance of conductive fluid by way of the measurement electrode. The program further causes the processor to determine a value of temperature based on the conductive fluid based on the impedance, and generate a plasma proximate to the active electrode.

A non-transitory computer-readable medium storing a program is disclosed. When the program is executed by a processor, the program causes the processor to determine a temperature of an electrically conductive fluid by causing the processor to cause a voltage to be applied across a measurement electrode and a return electrode disposed on a distal end of an electrosurgical wand. The program further causes the processor to measure impedance of conductive fluid by way of the measurement electrode and determine a value of temperature based on the conductive fluid based on the impedance.

BRIEF DESCRIPTION OF THE DRAWINGS

For a detailed description of exemplary embodiments, reference will now be made to the accompanying drawings in which.

NOTATION AND NOMENCLATURE

Figure 1:
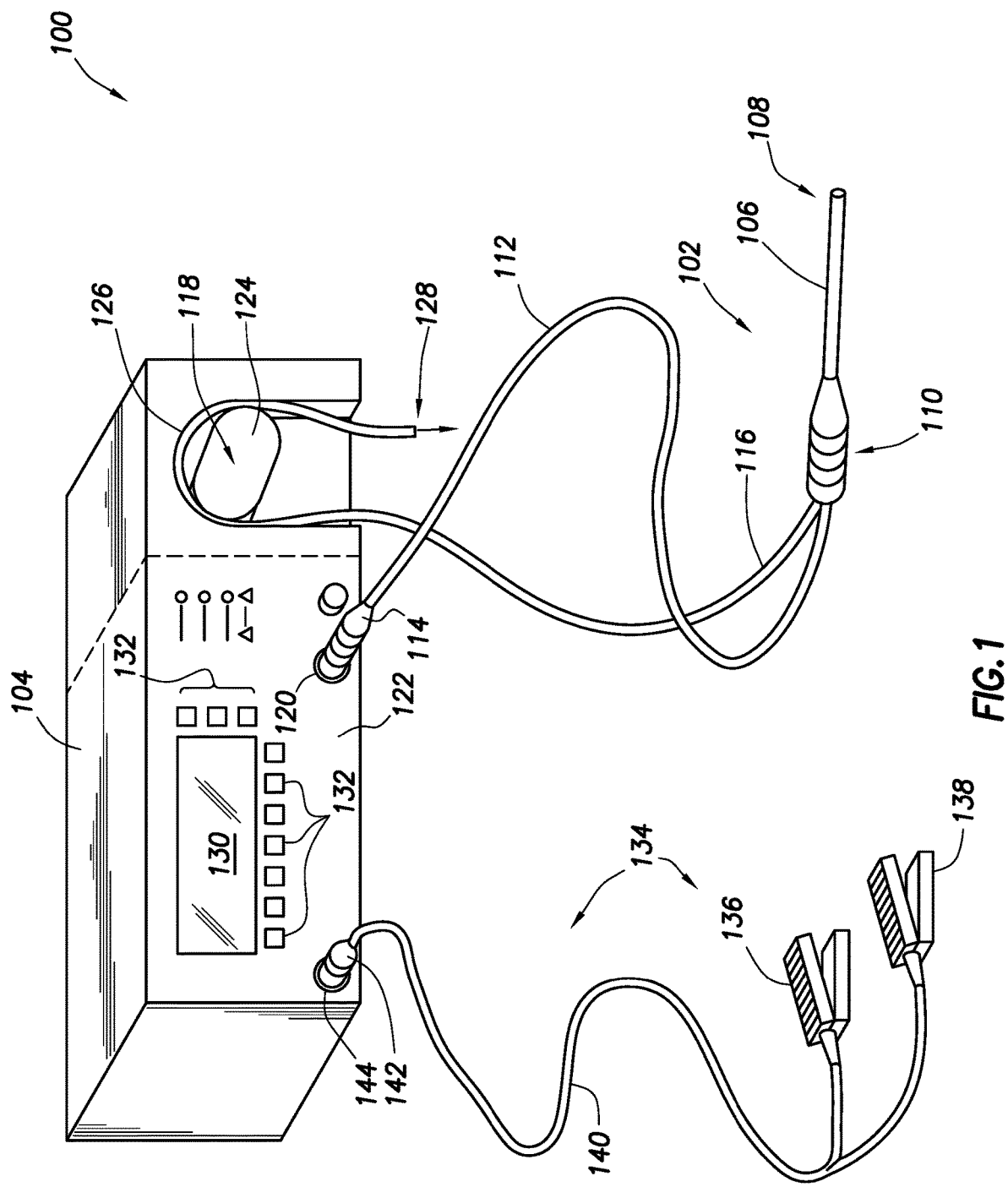
FIG. 1 shows an electrosurgical system in accordance with at least some embodiments.

Certain terms are used throughout the following description and claims to refer to particular system components. As one skilled in the art will appreciate, different companies may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

Reference to a singular item includes the possibility that there are plural of the same items present. More specifically, as used herein and in the appended claims, the singular forms "a," "an," "said" and "the" include plural references unless the context clearly dictates otherwise. It is further noted that the claims may be drafted to exclude any optional element. As such, this statement serves as antecedent basis for use of such exclusive terminology as "solely," "only" and the like in connection with the recitation of claim elements, or use of a "negative" limitation. Lastly, it is to be appreciated that unless defined otherwise, all technical and scientific terms used herein have the same meaning as commonly understood by one of ordinary skill in the art to which this invention belongs.

"Ablation" shall mean removal of tissue based on tissue interaction with a plasma.

"Active electrode" shall mean an electrode of an electrosurgical wand which produces an electrically-induced tissue-altering effect when brought into contact with, or close proximity to, a tissue targeted for treatment.

"Return electrode" shall mean an electrode of an electrosurgical wand which serves to provide a current flow path for electrical charges with respect to an active electrode, and/or an electrode of an electrical surgical wand which does not itself produce an electrically-induced tissue-altering effect on tissue targeted for treatment.

A fluid conduit said to be "within" an elongate shaft shall include not only a separate fluid conduit that physically resides within an internal volume of the elongate shaft, but also situations where the internal volume of the elongate shaft is itself the fluid conduit.

Where a range of values is provided, it is understood that every intervening value, between the upper and lower limit of that range and any other stated or intervening value in that state range is encompassed within the invention. Also, it is contemplated that any optional feature of the invention variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

DETAILED DESCRIPTION

The following discussion is directed to various embodiments. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

It is to be understood that this invention is not limited to particular variations set forth herein as various changes or modifications may be made, and equivalents may be substituted, without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the score or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

The various embodiments are directed to electrosurgical methods and related electrosurgical systems. In particular, the various embodiments are directed to an electrosurgical system having the means to measure a temperature of conductive fluid present in an area being treated. In various embodiments, if a temperature of the conductive fluid approaches a predetermined limit, adjustments may be made to operations of the electrosurgical system or other actions may be taken. For example, during an ablation procedure, ablation may be halted to give the conductive fluid time to cool and/or an increase to fluid flow may occur to exchange hot fluid for cooler fluid. As another example, an operator may be notified that damage may occur to the area being treated. It may be understood that, while embodiments of the disclosed temperature measurement method are discussed in the context of conductive fluid within a body cavity or joint, the discussed embodiments may be employed with any electrically conductive solution, without limit.

FIG. 1 illustrates an electrosurgical system 100 in accordance with at least some embodiments. In particular, the electrosurgical system 100 comprises an electrosurgical wand 102 (hereinafter "wand 102") coupled to an electrosurgical controller 104 (hereinafter "controller 104"). In some embodiments, the wand 102 may comprise a monopolar or bipolar radio frequency (RF) probe. The wand 102 comprises an elongate shaft 106 that defines distal end 108. The elongate shaft 106 further couples to a handle or proximal end 110, where a physician grips the wand 102 during surgical procedures. The wand 102 further comprises a flexible multi-conductor cable 112 housing one or more electrical leads (not specifically shown in FIG. 1), and the flexible multi-conductor cable 112 terminates in a wand connector 114. As shown in FIG. 1, the wand 102 couples to the controller 104, such as by a controller connector 120 on an outer surface of the enclosure 122 (in the illustrative case of FIG. 1, the front surface).

Though not visible in the view of FIG. 1, in some embodiments the wand 102 has one or more internal fluid conduits coupled to externally accessible tubular members. As illustrated, the wand 102 has a flexible tubular member 116, used to provide aspiration at the distal end 108 of the wand. In accordance with various embodiments, the tubular member 116 couples to a peristaltic pump 118, which peristaltic pump 118 is illustratively shown as an integral component with the controller 104 (i.e., residing at least partially within the enclosure 122 of the controller 104). In other embodiments, an enclosure for the peristaltic pump 118 may be separate from the enclosure 122 for the controller 104 (as shown by dashed lined in the figure), but in any event the peristaltic pump is operatively coupled to the controller 104.

The example peristaltic pump 118 comprises a rotor portion (hereafter just "rotor 124") as well as a stator portion 126 (hereafter just "stator 126"). The flexible tubular member 116 couples within the peristaltic pump 118 between the rotor 124 and the stator 126, and movement of the rotor 124 against the flexible tubular member 116 causes fluid movement toward the discharge 128. While the illustrative peristaltic pump 118 is shown with a two-head rotor 124, varying types of peristaltic pumps 118 may be used (e.g., a five-head peristaltic pump). In the context of the various embodiments, the peristaltic pump 118 creates a volume-controlled aspiration from a surgical field at the distal end 108 of the wand 102, with the control based on a speed of the rotor 124, as commended by the controller 104. In other cases, aspiration may be provided by any suitable vacuum source, such as wall suction available in most hospital situations, and thus the peristaltic pump 118 may be omitted in some cases.

Still referring to FIG. 1, a display device or interface device 130 is visible through the enclosure 122 of the controller 104, and in some embodiments a user may select operational modes of the controller 104 by way of the interface device 130 and related buttons 132.

In some embodiments the electrosurgical system 100 also comprises a foot pedal assembly 134. The foot pedal assembly 134 may comprise one or more pedal devices 136 and 138, a flexible multi-conductor cable 140 and a pedal connector 142. While only two pedal devices 136 and 138 are shown, one or more pedal devices may be implemented. The enclosure 122 of the controller 104 may comprise a corresponding connector 144 that couples to the pedal connector 142. A physician may use the foot pedal assembly 134 to control various aspects of the controller 104, such as the mode of ablation. For example, pedal device 136 may be used for on-off control of the application of radio frequency (RF) energy to the wand 102. In certain embodiments, control of the various operational or performance aspects of controller 104 may be activated by selectively depressing finger buttons located on handle 110 of wand 102 (the finger buttons not specifically shown so as not to unduly complicate the figure).

The electrosurgical system 100 of the various embodiments may employ COBLATION® technology. The COBLATION® technology may ablate carbon-based molecules with plasma formed from an application of radio frequency (RF) signal. In particular, the assignee of the present disclosure is the owner of COBLATION® technology. COBLATION® technology involves the application of a radio frequency (RF) signal between one or more active electrodes and one or more return electrodes of the wand 102 to develop high electric field intensities in the vicinity of the target tissue. The electric field intensities may be sufficient to vaporize an electrically conductive fluid over at least a portion of the one or more active electrodes in the region between the one or more active electrodes and the target tissue. The electrically conductive fluid may be inherently present in the body, such as blood, or in some cases extracellular or intracellular fluid. In other embodiments, the electrically conductive fluid may be a liquid or gas, such as isotonic saline. In some embodiments, such as surgical procedures involving a knee or shoulder, the electrically conductive fluid is delivered in the vicinity of the active electrode and/or to the target site by a delivery system separate and apart from the system 100.

When the electrically conductive fluid is heated to the point that the atoms of the fluid vaporize faster than the atoms recondense, a gas is formed. When sufficient energy is applied to the gas, the atoms collide with each other causes a release of electrons in the process, and an ionized gas or plasma is formed (to so-called "fourth state of matter"). Stated otherwise, plasmas may be formed by heating a gas and ionizing the gas by driving an electric current through the gas, or by directing electromagnetic waves into the gas. The methods of plasma formation give energy to free electrons in the plasma directly, electron-atom collisions liberate more electrons, and the process cascades until the desired degree of ionization is achieved. A more complete description of plasma can be found in Plasma Physics, by R. J. Goldston and P. H. Rutherford of the Plasma Physics Laboratory of Princeton University (1995), the complete disclosure of which is incorporated herein by reference.

As the density of the plasma becomes sufficiently low (i.e., less than approximately 1020 atoms/cm$^3$ for aqueous solutions), the electron mean free path increases such that subsequently injected electrons cause impact ionization within the plasma. When the ionic particles in the plasma layers have sufficient energy (e.g., 3.5 electron-Volt (eV) to 5 eV), collisions of the ionic particles with molecules that make up the target tissue break molecular bonds of the target tissue, dissociating molecules into free radicals which then combine into gaseous or liquid species. By means of the molecular dissociation (as opposed to thermal evaporation or carbonization), the target tissue is volumetrically removed through molecular dissociation of larger organic molecules into smaller molecules and/or atoms, such as hydrogen, oxygen, oxides of carbon, hydrocarbons and nitrogen compounds.

The molecular dissociation completely removes the tissue structure, as opposed to dehydrating the tissue material by the removal of liquid within the cells of the tissue and extracellular fluids, as occurs in related art electrosurgical desiccation and vaporization. A more detailed description of the molecular dissociation can be found in commonly assigned U.S. Pat. No. 5,697,882 the complete disclosure of which is incorporated herein by reference.

The energy density produced by electrosurgical system 100 at the distal end 108 of the wand 102 may be varied by adjusting a variety of factors, such as: the number of active electrodes; electrode size and spacing; electrode surface area; asperities and/or sharp edges on the electrode surfaces; electrode materials; applied voltage; current limiting of one or more electrodes (e.g., by placing an inductor in series with an electrode); electrical conductivity of the fluid in contact with the electrodes; density of the conductive fluid; and other factors. Accordingly, these factors can be manipulated to control the energy level of the excited electrons.

Since different tissue structures have different molecular bonds, the electrosurgical system 100 may be configured to produce energy sufficient to break the molecular bonds of certain tissue but insufficient to break the molecular bonds of other tissue. For example, fatty tissue (e.g., adipose) has double bonds that require an energy level higher than 4 eV to 5 eV (i.e., on the order of about 8 eV) to break. Accordingly, the COBLATION® technology in some modes of operation does not ablate such fatty tissue; however, the COBLATION® technology at the lower energy levels may be used to effectively ablate cells to release the inner fat content in a liquid form. Other modes of operation may have increased energy such that the double bonds can also be broken in a similar fashion as the single bonds (e.g., increasing voltage or changing the electrode configuration to increase the current density at the electrodes). A more complete description of the various phenomena can be found in commonly assigned U.S. Pat. Nos. 6,355,032, 6,149,120, 6,296,136, and 8,192,424 the complete disclosures of which are incorporated herein by reference. In various embodiments of the electrosurgical system 100, impedance at the electrode is (directly or indirectly) monitored and used as a parameter to control the volume flow rate of aspiration.

During an ablation or coagulation procedure as may be performed by the electrosurgical system 100, conductive fluid surrounding an electrode (i.e., an active electrode) on the distal end 108 or in the area being treated may be heated by the distal end 108 of the wand 102. High temperatures of the conductive fluid can damage living tissue in the area being treated. Measuring temperature of the conductive fluid around the active electrode may be difficult because access to conductive fluid may be limited by the geometry of the distal end 108, or space in an area being treated (e.g., joint space, cannula space, etc.). Temperature sensors (e.g., thermocouples, resistive thermal devices (RTDs)) embedded within or near an active electrode delivering an electric field in the vicinity of the targeted tissue may be problematic. For example, the electric field in the vicinity of the active electrode disrupts the temperature measurement (e.g., the electric field near the active electrode may induce electrical currents on the conductors associated with the temperature sensors, thus skewing the measurements).

In accordance with various embodiments, the distal end 108 of the wand 102 comprises a means to accurately measure the temperature of the conductive fluid present in an area targeted for treatment or undergoing treatment. In particular, by measuring an impedance of the conductive fluid between electrodes disposed near the distal end 108, a calculation may be made of the surrounding conductive fluid temperature. An impedance of the conductive fluid correlates to a temperature of the conductive fluid; the electrical impedance of the conductive fluid deceases with increasing conductive fluid temperature. For example, in a cold conductive fluid (e.g., 18° C.), an impedance of the conductive fluid may be relatively high, around 50 Ohms. When the conductive fluid temperature increases from 18° C. to 45° C. the impedance of the conductive fluid may decrease from 50 to 30 Ohms.

Figures 2A, 2B:
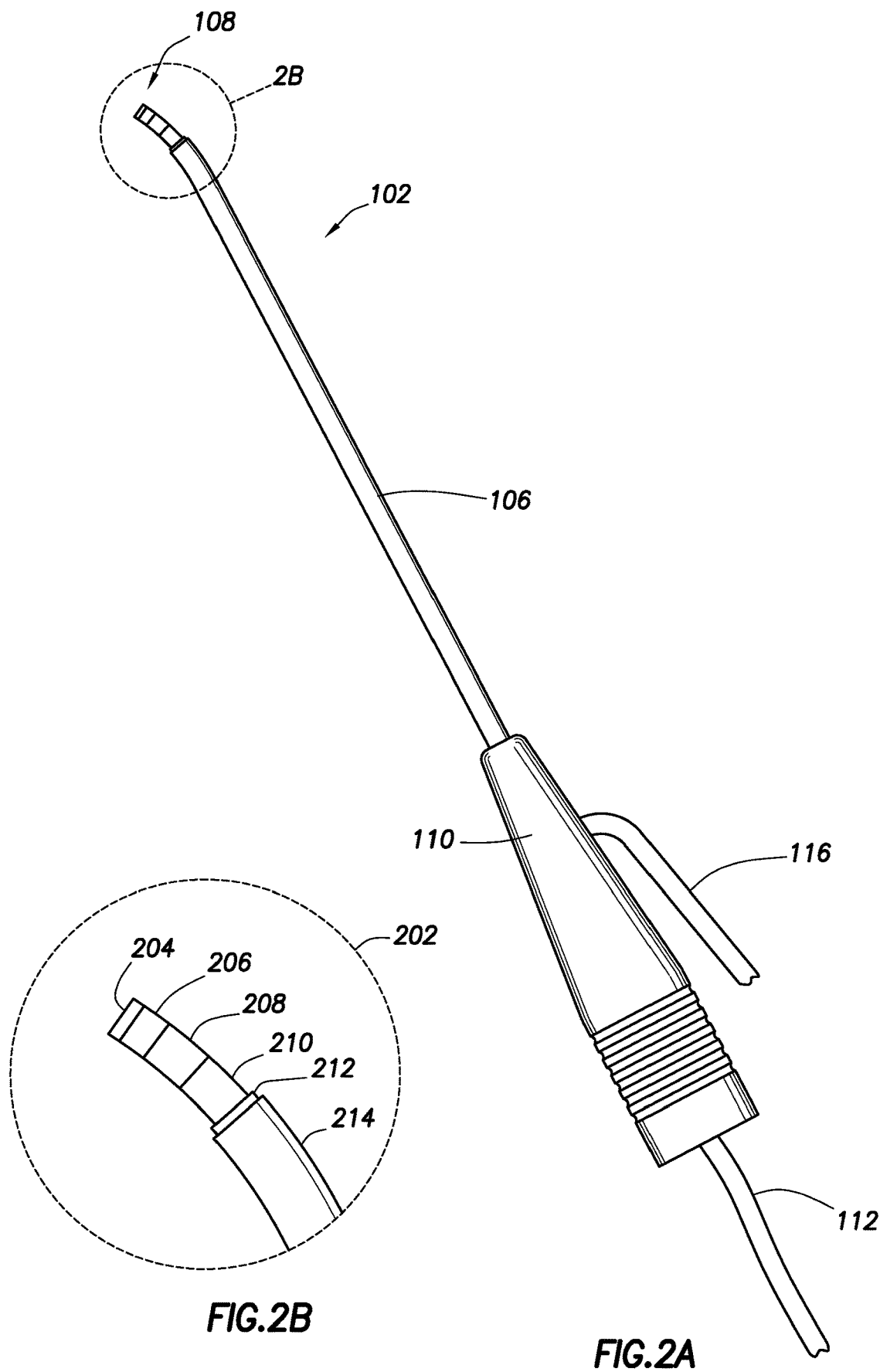
FIG. 2 shows an elevation view of an electrosurgical wand in accordance with at least some embodiments.

FIG. 2 shows an elevation view of wand 102 in accordance with example systems. In particular, wand 102 comprises elongate shaft 106 which may be flexible or rigid, a handle 110 coupled to the proximal end of the elongate shaft 106. Also visible in FIG. 2 is the flexible tubular member 116 extending from the wand 102 and the multi-conductor cable 112.

A magnified view 202 of distal end 108 is also shown in FIG. 2. The example wand 102 comprises an active electrode 204 disposed on the distal end 108 of the elongate shaft 106. Active electrode 204 may be coupled to an active or passive control network within controller 104 (FIG. 1) by means of one or more insulated electrical connectors (not shown) in the multi-conductor cable 112. The active electrode 204 is electrically isolated from common or return electrodes 208 by an insulator 206 which is disposed on the shaft proximally of the active electrode 204.

Disposed proximally from the distal tip and the active electrode, both the insulator 206 and return electrode 208 are concentric with the elongate shaft 106 of the wand 102. The insulator 206 may be composed of any electrically insulating material such as epoxy, plastic, ceramic, silicone, glass or the like. Proximally from the return electrode 208, another insulator 210 may be disposed concentric with the elongate shaft 106 of the wand 102. A measurement electrode 212 is proximally disposed from the insulator 210 and disposed concentric with the elongate shaft 106 of the wand 102. In this embodiment, the measurement electrode is distinct from both the active and return electrode, and the measurement electrode is exposed on an outside surface of the electrosurgical wand. Finally another insulator 214 may is disposed next to the measurement electrode 212.

The active electrode 204 may be in contact with tissue or bone during a procedure and otherwise unable to measure an impedance of conductive fluid around the active electrode 204 or near an area being treated. Accordingly, the measurement electrode 212 disposed proximally from the active electrode 204 but distinct from the active electrode 204 may measure an impedance of the conductive fluid proximal to the active electrode 204. During an impedance measurement a voltage may be applied across the measurement electrode 212 and the return electrode 208. In other embodiments, during periods of time when a plasma is not being created near the active electrode 204 the impedance measurement may be obtained by way of the active electrode 204 and the return electrode 208. In the example system of FIG. 2, the active electrode 204 and the measurement electrode 212 share a common return electrode 208.

Additionally, although a single electrode pair comprising the measurement electrode 212 and the return electrode 208 is shown, some embodiments may include measuring impedance between multiple pairs of electrodes. Thus, multiple pairs of electrodes may be present at the distal end 108 of the wand 102 or on other portions of the wand 102. Assuming that the position of the respective electrode pairs is different, the conduction pathway between each electrode pair is not the same and can provide additional information. In one aspect, under circumstances where the temperature of the conductive fluid is expected to change with position, the relative location of conduction pathways between respective electrode pairs can be used to provide spatial information. In another aspect, under circumstances where the temperature of the conductive fluid is not expected to change with position, impedance measurement made between a given electrode pair may be ignored if differing significantly from contemporaneous impedance measurement made between other electrode pairs.

Figure 3:
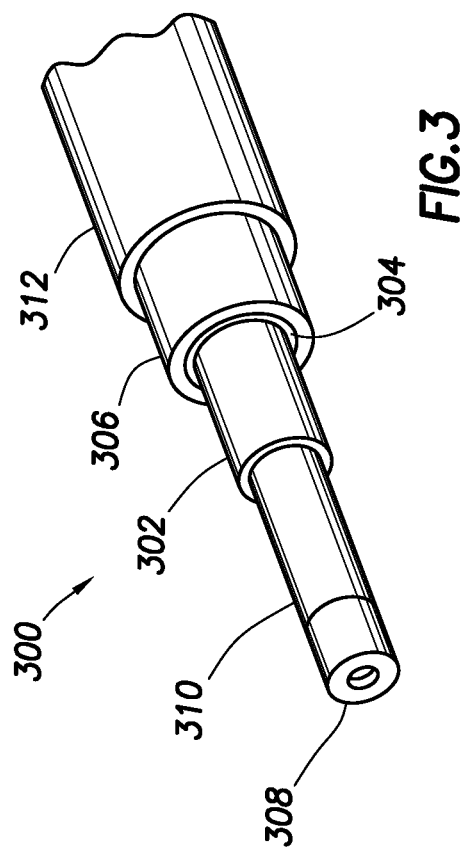
FIG. 3 shows a perspective view of a distal end of an electrosurgical wand in accordance with at least some embodiments.

FIG. 3 shows a perspective view 300 of the distal end 108 of another example electrosurgical wand 102. As shown, return electrode 302 is disposed proximally to insulator 304. Measurement electrode 306 is exposed on an outside surface of the wand 102. In various embodiments, measurement electrode 306 may fully or partially circumscribe return electrode 302. The insulator 304 may be sandwiched between the return electrode 302 and the measurement electrode 306. Thus, the insulator 304 may fully circumscribe return electrode 302 when the measurement electrode 306 fully circumscribes the return electrode 302. In embodiments, where the measurement electrode 306 partially circumscribes the return electrode 302, the insulator 304 may also partially circumscribe the return electrode 302 such that it is disposed between the return electrode 302 and a measurement electrode 306.

An insulator 310 is disposed proximally and adjacent to the measurement electrode 306. The insulator 310 may circumscribe the return electrode 306 and extend along an axial length of the wand 102. Additionally, an active electrode 308 is disposed at the distal tip of the distal end 108 of the wand 102. An insulator 310 is disposed proximally to the active electrode 308; insulator 310 is disposed between the active electrode 308 and the return electrode 302.

During an impedance measurement, a voltage may be induced between the measurement electrode 306 and the return electrode 302, by a controller electrically coupled to the wand 102. A current flowing along a path comprising the measurement electrode 306 and the return electrode 302 may be measured by the controller and an impedance may be calculated by the controller based on the measured current flow.

Figure 4:
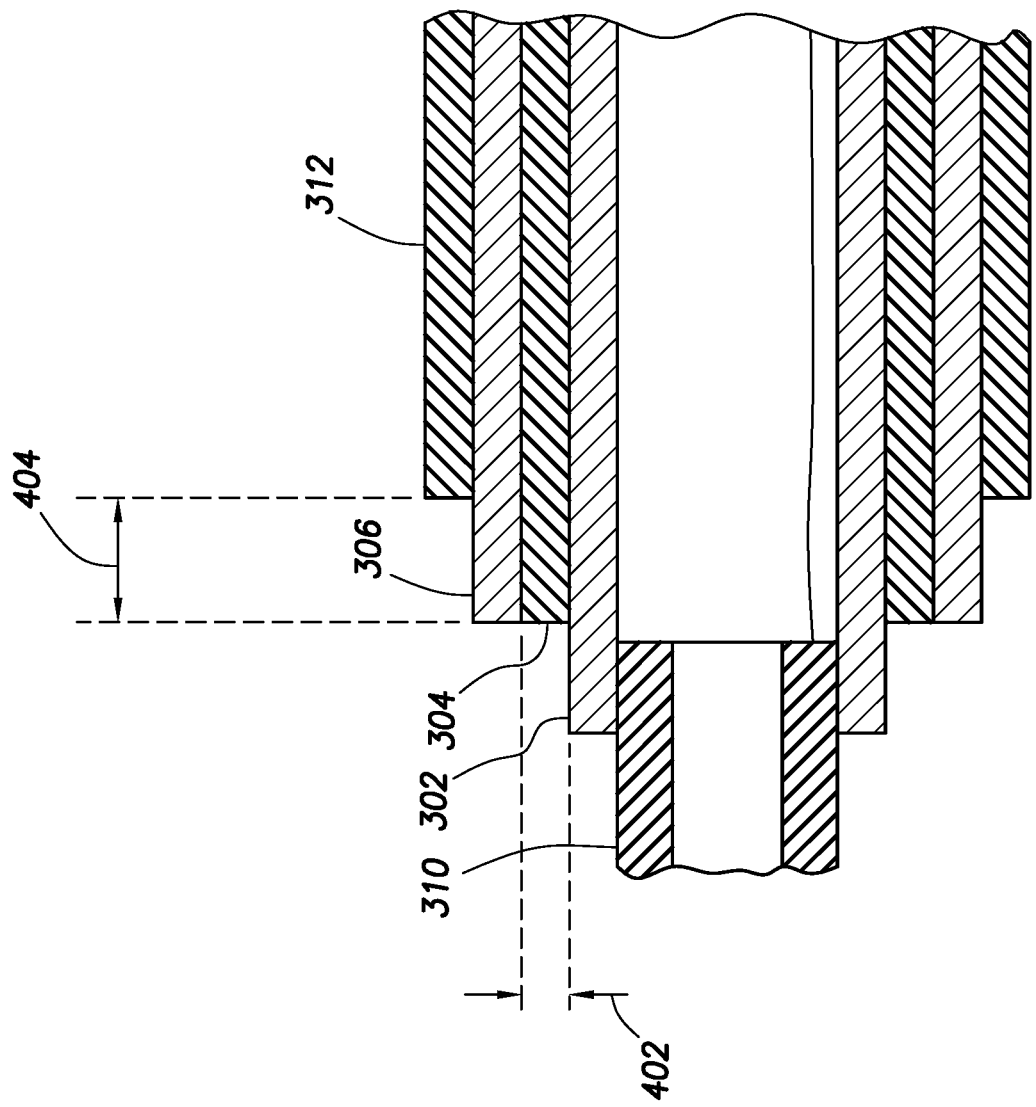
FIG. 4 shows a cross-sectional elevation view of a portion of an electrosurgical wand in accordance with at least some embodiments.

FIG. 4 shows a cross-sectional elevation view of a portion of the wand 102 of FIG. 3. FIG. 4 shows a portion of the wand 102 starting at the distal end 108 comprising the insulator 310 and extending away from the distal tip toward the proximal end 110 including the return electrode 302, insulator 304, measurement electrode 306, and insulator 312. As shown, insulator 310 may not extend along the entire axial length of the wand 102, but overlap a portion of return electrode 302. Insulator 304, is sandwiched between return electrode 302 and measurement electrode 306. Insulator 304 extends at least along portions in which return electrode 302 and measurement electrode 306 overlap within the wand 102 such that the electrodes 302 and 306 are isolated from each other. Insulator 312 extends along the axial length of the wand 102 overlaps a portion of the measurement electrode 306 such that a portion of the measurement electrode 306 is exposed on an outside surface of the electrosurgical wand 102. In FIG. 4, a thickness 402 of the insulator may be 0.228 millimeters (mm). Additionally, an exposed portion 404 of the measurement electrode may be 1 mm.

Figure 5:
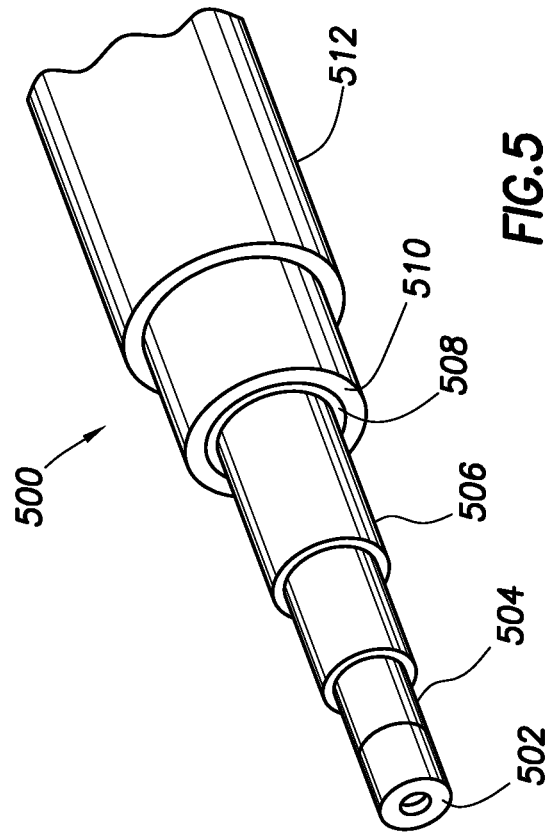
FIG. 5 shows a perspective view of a distal end of an electrosurgical wand in accordance with at least some embodiments.

FIG. 5 shows a perspective view 500 of a distal end of the electrosurgical wand in accordance with yet still other embodiments. The embodiment in FIG. 5 comprises separate electrodes for the active electrode 502 and the measurement electrode 510. FIG. 5 shows a portion of the distal end 108 starting at the distal tip comprising the active electrode 502 and extending away from the distal tip toward the proximal end 110 including a return electrode 504, another return electrode 506, an insulator 508, a measurement electrode 510, and an insulator 512.

In FIG. 5, the return electrode 504 that is paired with the active electrode 502 is disposed proximally to the active electrode 502. Further along the distal end 108 away from the distal tip, a return electrode 506 is disposed proximally to the measurement electrode 510. Return electrode 506 may be paired with the measurement electrode 510 where a current flowing along a path comprising the electrodes 506 and 510 may be measured to calculate an impedance value. An insulator 508 is sandwiched between the return electrode 506 and the measurement electrode 510. Insulator 512 is disposed proximally to and wraps around the measurement electrode 510 and extends along the axial length of the wand 102.

Figure 6:
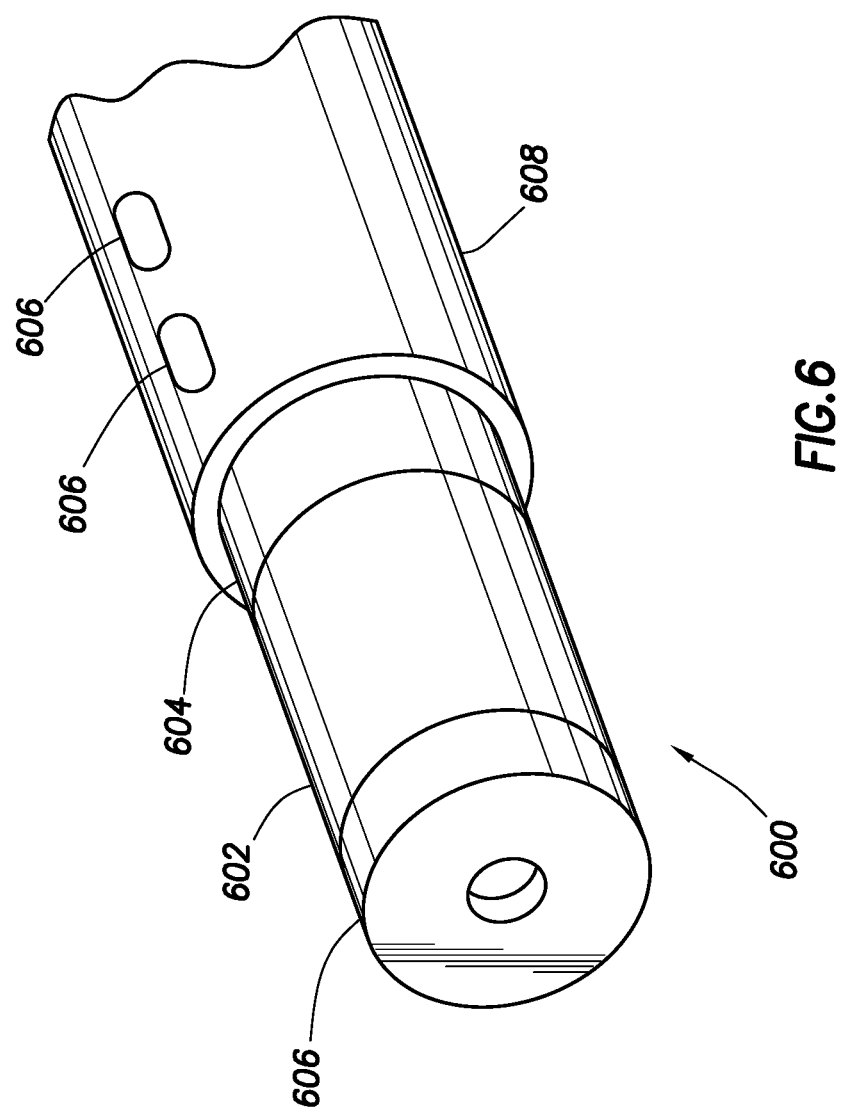
FIG. 6 shows a perspective view of a distal end of an electrosurgical wand in accordance with at least some embodiments.

FIG. 6 shows a perspective view 600 of a distal end of an electrosurgical wand 102 in accordance with yet still other embodiments. FIG. 6 depicts the distal end of wand 102 comprising button electrodes 606 that are spaced apart and adjacent to each other on the distal end 108 of the wand 102. Of the button electrodes 600, one button electrode may be a measurement electrode while the other is a return electrode. The electrodes 606 may be spaced apart and exposed on an outer surface 608 of the wand 102. In some embodiments, the electrodes 606 may be spaced apart and protrude perpendicularly from the outer surface 608 of the wand 102 such that a conductive fluid may reside between the button electrodes 606 when the button electrodes 606 are submerged fully or partially in the conductive fluid.

Additionally, at the distal end 108 of the wand 102 an insulator 602 may be disposed proximally to the distal tip comprising the active electrode 606. A return electrode 604 for the active electrode 606 may be disposed proximally to the active electrode 606 and further along the distal end away from the distal tip. In various embodiments, the active electrode 606 may be in touch with tissue or the target area for treatment. The conductive fluid surrounds the tissue or targeted area for treatment in contact with the active electrode 606. The button electrodes 606 comprising a return electrode and a measurement electrode is distinct from the active electrode, as shown so as to measure conductive fluid surrounding the tissue and not an impedance of the tissue or targeted area in contact with the active electrode 606.

Figure 7:
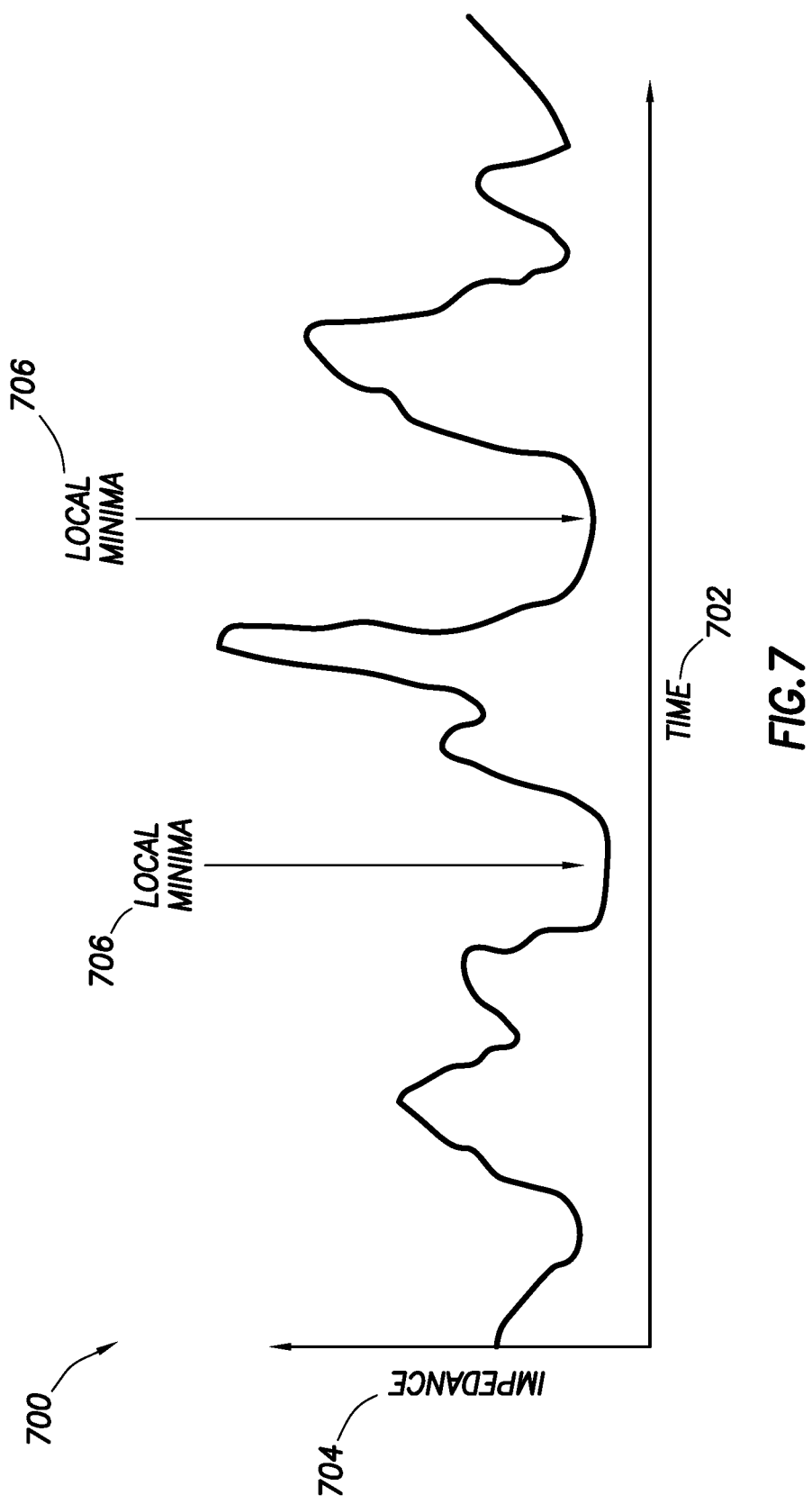
FIG. 7 shows an example graph relating measured impedance values over time.

FIG. 7 shows an example impedance-time graph 700 relating measured impedance values over time. Impedance values 704 are tracked along the y-axis while time 702 is shown along the x-axis. During a procedure, various impedance measurements may be taken by the electrosurgical system 100. An operator, such as a physician may move the wand 102 or more specifically the distal end 108 to different locations within a cavity comprising the tissue and conductive fluid. The plurality of impedance measurements may be used to determine the impedance of the conductive fluid. An impedance measurement obtained by the measurement electrode of an electrode pair, when the measurement electrode is touching tissue, may be higher than when the electrode pair only has conductive fluid between them without touching anything else.

In other embodiments, the wand 102 may comprise a plurality of pairs of electrodes. A wand 102 may measure different impedances in different locations in the cavity depending on what is present between a pair of electrodes used to measure impedance. The electrosurgical system 100 is capable of measuring voltage or electrical flow from the electrode pair by way of an electrosurgical controller and calculating an impedance from the measured values.

Thus, in one embodiment, several impedance measurement may be obtained over time as a physician moves a wand around in a cavity. Given several impedance measurements, values below a certain threshold may be indicative of impedance of the conductive fluid, whereas value above the threshold may be indicative of impedance value of the conductive fluid in conjunction with surrounding tissue or other material in the vicinity of the conductive fluid.

In some embodiments, one or more selected portions of the measured impedance-time graph 700 may be used to determine temperature. As mentioned above, the impedance of the conductive fluid is expected to be less than that of tissue or bone. Higher impedances and/or rapid changes within the measured-impedance-time response may arise due to a portion of the electrode pair comprising the measurement electrode, coming into or out of contact with tissue or bone, rather than changes in temperature of the conductive fluid. Conversely, lower impedance measurements within the impedance-time graph 700 may be attributed to impedance measurements of the conductive fluid alone.

Accordingly, temperature may be determined from impedance values that fall below a predetermined threshold within the impedance-time graph 700 (e.g. as discrete impedance measurements or an aggregate of values below the predetermined threshold), rather than the entire response. For example, a local minima 706 may be calculated from the impedance-time graph 700 and the local minima 706 may be correlated to a temperature of the conductive fluid. In another embodiment, an average of one or more values below a predetermined threshold may be calculated and the average may be correlated to a temperature of the conductive fluid.

Figure 8:
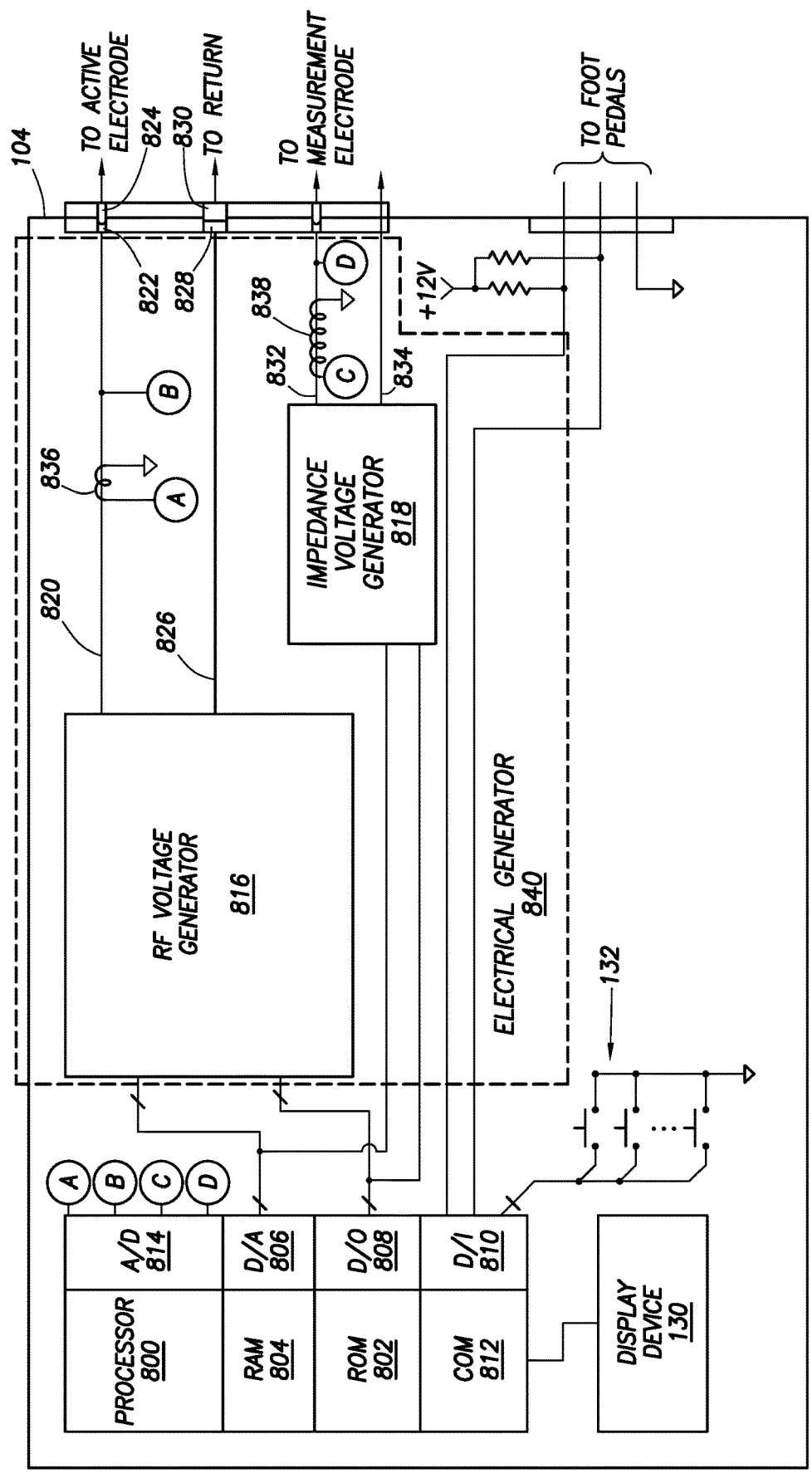
FIG. 8 shows an electrical bock diagram of a controller in accordance with at least some embodiments.

FIG. 8 shows an electrical block diagram of controller 104 in accordance with at least some embodiments. In particular, the controller 104 comprises a processor 800. The processor 800 may be a microcontroller, and therefore the microcontroller may be integral with read-only memory (ROM) 802, random access memory (RAM) 804, digital-to-analog converter (D/A) 806, analog-to-digital converter (A/D) 814, digital outputs (D/O) 808, and digital inputs (D/I) 810. The processor 800 may further provide one or more externally available peripheral buses, such as a serial bus (e.g., I²C), parallel bus, or other bus and corresponding communication mode. The processor 800 may further be integral with communication logic 812 to enable the processor 800 to communicate with external devices, as well as internal devices, such as display device 130. Although in some embodiments the processor 800 may be implemented in the form of a microcontroller, in other embodiments the processor 800 may be implemented as a standalone central processing unit in combination with individual RAM, ROM, communication, A/D, D/A, D/O, and D/I devices, as well as communication hardware for communication to peripheral components.

ROM 802 stores instructions executable by the processor 800. In particular, the ROM 802 may comprise a software program that, when executed, causes the controller to control ablation, including in some cases increasing and decreasing peristaltic pump speed responsive to various feedback parameters. The RAM 804 may be the working memory for the processor 800, where data may be temporarily stored and from which instructions may be executed. Processor 800 couples to other devices within the controller 104 by way of the digital-to-analog converter 806 (e.g., in some embodiment the plasma generator which may be referred to as the RF voltage generator 816 and/or the impedance voltage generator 818), digital outputs 808 (e.g., in some embodiment the RF voltage generator 816 and/or the impedance voltage generator 818), digital inputs 810 (e.g., interface devices such as push button switches 132 or foot pedal assembly 134 (FIG. 1)), and communication device 812 (e.g., display device 130).

Electrical generator 840 provides RF energy to create plasma and measure voltage and current (from which impedance is calculated). Electrical generator 840 generates an alternating current (AC) voltage signal that is coupled to active electrode 204 of the wand 102 and measurement electrode 212 of the wand 102. In some embodiments, the electrical generator 840 is comprised of two separate generators, an RF voltage generator 816 (i.e., plasma generator) and an impedance voltage generator 818. In some embodiments, the functionality of the impedance voltage generator 818 may be integrated into the RF voltage generator 816 and thus the impedance voltage generator 818 may be an optional component of the electrical generator 840.

Voltage generator 816 generates an alternating current (AC) voltage signal that is coupled to active electrode 204 of the wand 102. In some embodiments, the voltage generator defines an active terminal 820 which couples to electrical pin 822 in the controller connector 120, electrical pin 824 in the wand connector 114, and ultimately to the active electrode (e.g., active electrode 204, 308, 502). Likewise, the voltage generator defines a return terminal 826 which couples to electrical pin 828 in the controller connector 120, electrical pin 830 in the wand connector 114, and ultimately to the return electrode paired with the active electrode (e.g., return electrode 208, 302, 504).

Additional active terminals and/or return terminals may be used. For example, an additional active and return terminal may be used to connect to the measurement electrode (e.g., measurement electrode 306 or 510) and a return electrode (e.g., return electrode 302 or 504). In some embodiments, the impedance voltage generator 818 may be used to generate an alternating current (AC) voltage signal that is coupled to a measurement electrode (e.g., measurement electrode 306 or 510).

The active terminal 820 and impedance terminal 832 are the terminals upon which the voltages and electrical currents are induced by the voltage generator 816 and the impedance voltage generator 818, respectively. And the return terminals 826 and 834 provide a return path for electrical currents. It would be possible for the return terminals 826 and 834 to provide a common or ground being the same as the common or ground within the balance of the controller 104 (e.g., the common 812 used on push-buttons 132), but in other embodiments the voltage generator 516 may be electrically "floated" from the balance of the controller 104, and thus the return terminal 524, when measured with respect to the common or earth ground (e.g., common 530) may show a voltage; however, an electrically floated voltage generators 816 or 818 and thus the potential for voltage readings on the return terminals 826 or 834 relative to earth ground does not negate the return terminal status of the terminal 826 relative to the active terminal 820 or the return terminal status of the return terminal 834 relative to the impedance terminal 832.

The AC voltage signal generated and applied between the active terminal 820 and the return terminal 826 by the voltage generator 816 is RF energy. Similarly, in embodiments comprising the impedance voltage generator 818, the AC voltage signal generated and applied between the impedance terminal 832 and the return terminal 834 by the impedance voltage generator 818 is RF energy. The voltage and current generated by voltage generators 816 and/or 818 may be delivered in a series of voltage pulses or AC voltage with a sufficiently high frequency such that the voltage is effectively applied continuously. However, RF energy provided by the RF voltage generator 816 may be of sufficient voltage and current to create a plasma or treat tissue near the active electrode. By contrast, the voltage and current provided by the impedance voltage generator 818 has lower voltage, current or time, sufficient to create a current flow and from which impedance can be calculated, but not of sufficient voltage, current, and/or time to instantiate a plasma or alter tissue between the measurement and return electrode.

Still referring to FIG. 8, in some embodiments the controller 104 further comprises a mechanism to sense the electrical current provided to the active electrode and/or the measurement electrode. In the illustrative case of FIG. 3, sensing current provided to the active electrode may be by way of a current sense transformer 836. Similarly, sensing current provided to the measurement electrode may be by way of a current sense transformer 838 with respect to the impedance terminal 832 of the impedance voltage generator 818 or the current sense transformer 836 in the event that an impedance voltage generator 818 is not implemented. In embodiments where the current sense transformer 836 is used to sense current provided to the measurement electrode, additional circuitry (e.g., switches and relays) may be used to direct the voltage/current (which would be different from the voltage/current being applied to generate plasma) to the measurement electrode. The sensing current may be used to measure an impedance detected between two electrodes. Accordingly, an impedance measuring portion may comprise a voltage generator and the switches, relays, transformers, etc. to detect a sensing current that is used to measure an impedance (e.g., impedance voltage generator 818, impedance terminal 832, return terminal 834, current sense transformer 838, etc.)

In particular, example current sense transformer 836 may have a conductor of the active terminal 820 threaded through the transformer such that the active terminal 820 becomes a single turn primary. Current flow in the single turn primary induces corresponding voltages and/or currents in the secondary. Thus, the illustrative current sense transformer 836 is coupled to the analog-to-digital converter 514 (as shown by the bubble A). Similarly, in embodiments in which the impedance voltage generator 818 is implemented, current sense transformer 838 may have a conductor of the impedance terminal 832 threaded through the transformer such that the impedance terminal 832 becomes a single turn primary. The illustrative current sense transformer 838 is coupled to the analog-to-digital converter 814 (as shown by bubble C). In some cases, either current sense transformer (836 and/or 838) may couple directly to the analog-to-digital converter 514, and in other cases additional circuitry may be imposed between either current sense transformer and the digital-to-analog converter 814, such as amplification circuits and protection circuits.

For example, in one example system the current sense transformer 836 is coupled to an integrated circuit device that takes the indication of current from the current sense transformer 836, calculates a root-mean-square (RMS) current value, and provides the RMS current values to the processor 800 through any suitable communication system (e.g., as an analog value applied to the ND 814, as a digital value applied to the multiple inputs of the D/I 810, as a packet message through the communication port 812). The current sense transformer is merely illustrative of any suitable mechanism to sense the current supplied to the active electrode, and other systems are possible. For example, a small resistor may be placed in series with the active terminal 820, and the voltage drop induced across the resistor used as an indication of the electrical current.

In another example, equally applicable to the impedance voltage generator 818, given that the voltage generator 816 is electrically floated, the mechanism to sense current is not limited to just the active terminal 820. Thus, in yet still further embodiments, the mechanism to sense current may be implemented with respect to the return terminal 826. For example, illustrative current sense transformer 836 may be implemented on a conductor associated with the return terminal 826.

In some example systems, the feedback parameter used by the processor 800 regarding the voltage generator 816 or the impedance voltage generator 818 is the electrical current flow. For example, in systems where the voltage generator or the impedance voltage generator can accurately produce an output voltage independent of the impedance of the attached load, the processor 800 having set point control for the voltage created by the voltage generator 816 or the impedance voltage generator 818 may be sufficient (e.g., to calculate a value indicative of impedance of the electrode circuit and plasma proximate the active electrode). However, in other cases, voltage too may be a feedback parameter (e.g., for calculating impedance). Thus, in some cases the active terminal 820 or the impedance terminal 832 may be electrically coupled to the digital-to-analog converter 806 (as shown by bubble B and D).

However, additional circuitry may be imposed between the active terminal 820 to 826 and the digital-to-analog converter 806, for example, various step-down transformers, protection circuits, and circuits to account for the electrically floated nature of the voltage generator 816 or impedance voltage generator 818. In yet still other cases, voltage sense circuitry may measure the voltage, and the measured voltage values may be provided other than by analog signal, such as by way of packet-based communications over the communication port 812.

Accordingly, in various embodiments, the processor 800 may process or receive voltage and/or current by way of A/D 814, from which the processor 800 may proceed to calculate impedance of conductive fluid by way of the measurement electrode. The processor 800 may further correlate measured impedance to a value of temperature of the conductive fluid based on the impedance.

Figure 9:
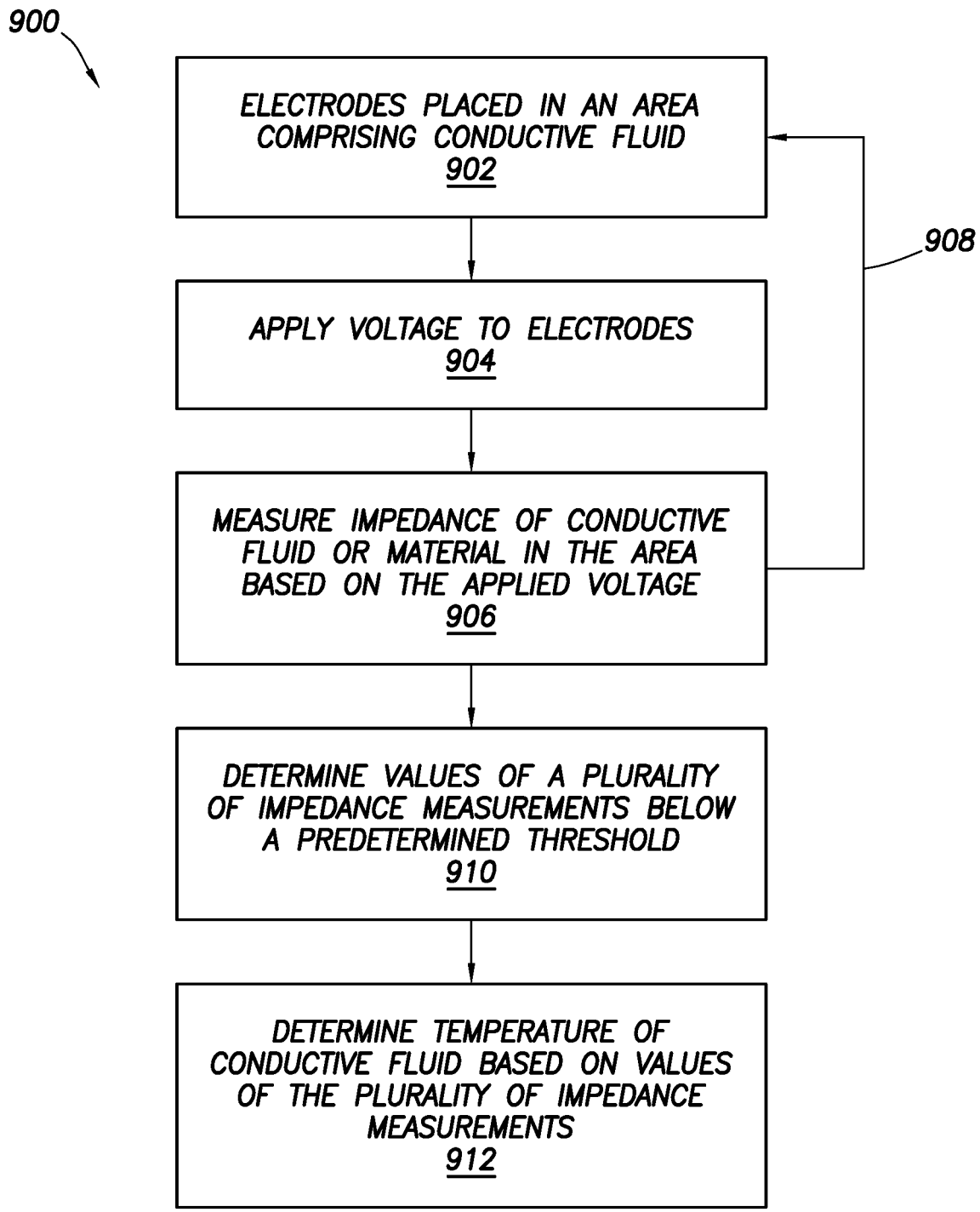
FIG. 9 shows a method in accordance with at least some embodiments.

FIG. 9 shows a method in accordance with at least some embodiments. In various embodiments, some of the blocks shown in FIG. 9 may be performed concurrently, in a different order than shown, or omitted. Additional method elements may be performed as desired. Additional method elements may be performed as desired.

At block 902, electrodes are placed in an area comprising conductive fluid (such as a body cavity or joint space). At block 904 a voltage is applied to the electrodes. At block 906, impedance of the conductive fluid or material in the area is measure based on the applied voltage and/or electrical current. In various embodiments, the method may go through several iterations of blocks 902 through 906 to obtain a plurality of impedance values. At block 910, a determination is made of values of the plurality of impedance measurements that are below a predetermined threshold. At block 912, a temperature of the conductive fluid is determined based on the values of the plurality of impedance measurements.

The above discussion is meant to be illustrative of the principles and various embodiments. Numerous variations and modifications will become apparent to those skilled in the art once the above disclosure is fully appreciated. It is intended that the following claims be interpreted to embrace all such variations and modifications.

While preferred embodiments of this disclosure have been shown and described, modifications thereof can be made by one skilled in the art without departing from the scope or teaching herein. The embodiments described herein are exemplary only and are not limiting. Because many varying and different embodiments may be made within the scope of the present inventive concept, including equivalent structures, materials, or methods hereafter thought of, and because many modifications may be made in the embodiments herein detailed in accordance with the descriptive requirements of the law, it is to be understood that the details herein are to be interpreted as illustrative and not in a limiting sense.

What is claimed is:

1. A method comprising:
   immersing electrodes disposed on a distal end of an electrosurgical wand, the immersing in a conductive fluid contained within a cavity having walls of a first material, the conductive fluid different than the first material, and the electrodes comprising an active electrode, a first electrode and a second electrode;
   placing the active electrode adjacent a target tissue associated with the first material and electrosurgically treating the target tissue with the active electrode;
   applying a voltage across the first electrode and the second electrode, the first and second electrode spaced apart on the distal end of the wand such that the conductive fluid resides between the first and second electrodes;
   measuring an impedance of the conductive fluid between the first and second electrodes, the first and second electrodes both proximally spaced from the active electrode and thereby proximally spaced away from the target tissue; and correlating a value of the measured impedance that is at or below a predetermined threshold impedance to a value of an impedance of the conductive fluid alone in contact with the first and second electrode; and determining temperature of the conductive fluid based on the value at or below the predetermined threshold impedance.

2. The method of claim 1, further comprising:

forming plasma proximate to the active electrode, the plasma created based on voltage applied to the active electrode; and ablating carbon-based molecules with the plasma.

3. The method of claim 1, further comprising:

moving the first and second electrodes to a plurality of locations within the cavity;

applying the voltage across the first and second electrodes at each location of the plurality of locations;

measuring a plurality of values of impedance corresponding to each location of the plurality of locations; and correlating values of the plurality of values of impedance below the predetermined threshold impedance to a temperature of the conductive fluid, the predetermined threshold impedance indicative of impedance values attributed to the conductive fluid only.

4. The method of claim 3, wherein correlating the values of the plurality of values below the predetermined threshold impedance further comprises: calculating an average of one of more of the values of the plurality of values; and correlating the average to temperature of the conductive fluid.

5. The method of claim 1, wherein immersing the electrodes further comprises immersing the electrodes such that the first electrode partially circumscribes the second electrode, wherein the second electrode extends along an axial length of the electrosurgical wand, and wherein an insulator is disposed between a portion of the first electrode and the second electrode.

6. The method of claim 5, further comprising contacting the active electrode distinct from the first and second electrode with the first material during the measurement of the impedance between the first and second electrodes.

7. The method claim 1, wherein immersing the electrodes further comprises immersing the electrodes such that the first and second electrodes comprise button electrodes and the button electrodes are spaced apart and adjacent to each other on the distal end of the electrosurgical wand.

8. An electrosurgical system comprising:

an electrosurgical wand comprising:

an active electrode disposed on a distal end of the electrosurgical wand;

a return electrode disposed on the distal end of the electrosurgical wand, the return electrode disposed proximally from the active electrode;

a measurement electrode disposed at the distal end of the electrosurgical wand, the measurement electrode distinct from and spaced away from both the active and the return electrodes, and configured to measure an impedance of conductive fluid contained within a joint cavity, the measurement electrode exposed on an outside surface of the electrosurgical wand; and an insulator disposed between a portion of the return electrode and the measurement electrode; and an electrosurgical controller electrically coupled to the electrosurgical wand, the electrosurgical controller comprising:

a processor;

a memory coupled to the processor;

an electrical generator operatively coupled to the processor, the electrical generator defines an active terminal, an impedance terminal, and a return terminal, the impedance terminal coupled to the measurement electrode, the return terminal coupled to the return electrode, and the active terminal coupled to the active electrode, the electrical generator configured to provide controllable voltage to the active, return and measurement electrodes;

the memory storing a program that, when executed by the processor, causes the processor to:

measure an impedance of the conductive fluid within the joint cavity by way of the measurement electrode;

determine a value of temperature of the conductive fluid based on a value of the impedance measured at or below a predetermined impedance threshold, wherein the predetermined impedance threshold is indicative that only conductive fluid is in contact with the measurement electrode; and generate a plasma proximate to the active electrode.

9. The electrosurgical system of claim 8, wherein the electrosurgical controller further comprises:

a plasma generator portion coupled to the active electrode, the plasma generator portion configured to create the plasma proximate to the active electrode; and an impedance measuring portion coupled to the measurement electrode, the impedance measuring portion configured to provide energy to the measurement electrode for measuring the impedance.

10. The electrosurgical system of claim 8, wherein when the program measures the impedance of the conductive fluid, the program causes the processor to:

measure a plurality of values of impedance; and correlate values of the plurality of values of impedance below the predetermined impedance threshold to the value of temperature of the conductive fluid, wherein the predetermined impedance threshold is indicative of the conductive fluid alone.

11. The electrosurgical system of claim 10, wherein when the program correlates the values of the plurality of values below the predetermined threshold impedance, the program causes the processor to:

calculate an average of one or more of the values of the plurality of values; and correlate the average to the value of temperature of the conductive fluid.

12. The electrosurgical system of claim 10, wherein the measurement and return electrodes comprise button electrodes spaced apart and adjacent to each other on the distal end of the electrosurgical wand.

13. The electrosurgical system of claim 8, wherein the electrosurgical wand further comprises:

the measurement electrode partially circumscribes the return electrode; and the return electrode extends along an axial length of the electrosurgical wand.

14. A non-transitory computer-readable medium storing a program, that when executed by a processor, causes the processor to determine a temperature of an electrically conductive fluid by causing the processor to:

apply a voltage across a measurement electrode and a return electrode disposed on a distal end of an electrosurgical wand;

measure an impedance of the conductive fluid by way of the measurement electrode;

wherein the impedance measured below a predetermined impedance threshold is indicative that the conductive fluid only is in contact with the measurement electrode; and determine a value of temperature of the conductive fluid based on the impedance measured below the predetermined impedance threshold.

15. The non-transitory computer-readable medium of claim 14, wherein when the program measures the impedance of the conductive fluid, the program causes the processor to:

measure a plurality of values of impedance; and correlate values of the plurality of values below the predetermined threshold impedance to a temperature of the conductive fluid only.

16. The non-transitory computer-readable medium of claim 15, wherein when the program correlates the values of the plurality of values below the predetermined threshold impedance, the program causes the processor to:

calculate an average of the one or more values of the plurality of values; and correlate the average to the temperature of the conductive fluid.

17. The non-transitory computer-readable medium of claim 14, wherein the program further causes the processor to:

cause a plasma to be formed proximate to an active electrode distinct from the measurement electrode and the return electrode, the plasma created based on voltage applied to the active electrode; and cause carbon-based molecules to be ablated with the plasma.

18. The non-transitory computer-readable medium of claim 14, wherein the program further cause the processor to:

cause a plasma to be formed proximate to an active electrode.

* * * * *